(12) United States Patent
Sprecker et al.

(10) Patent No.: US 6,596,686 B2
(45) Date of Patent: Jul. 22, 2003

(54) USE OF DIHYDROPYRANS AS FRAGRANCE MATERIAL

(75) Inventors: Mark A. Sprecker, Sea Bright, NJ (US); Charles E. J. Beck, Summit, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 268 days.

(21) Appl. No.: 09/804,321

(22) Filed: Mar. 12, 2001

(65) Prior Publication Data

US 2002/0173444 A1 Nov. 21, 2002

(51) Int. Cl.$^7$ .................................................. A61K 7/46
(52) U.S. Cl. ............................ 512/20; 512/25; 512/26; 512/27; 512/8; 512/11
(58) Field of Search .............................. 512/20, 25, 26, 512/27, 8, 11

(56) References Cited

U.S. PATENT DOCUMENTS

| | | | |
|---|---|---|---|
| 3,455,957 A | * | 7/1969 | Cahn et al. ................. 549/356 |
| 4,107,289 A | * | 8/1978 | Kaufman ..................... 424/45 |
| 5,162,551 A | * | 11/1992 | Broekhof et al. ........... 549/356 |
| 5,378,685 A | * | 1/1995 | Sprecker et al. ............. 512/11 |
| 5,492,933 A | | 2/1996 | Gray et al. |
| 5,508,279 A | | 4/1996 | Gray, II |
| 5,510,352 A | | 4/1996 | Gray, III |
| 5,532,278 A | | 7/1996 | Aberg et al. |
| 5,545,745 A | | 8/1996 | Gao et al. |
| 5,561,151 A | | 10/1996 | Young, I et al. |
| 5,571,827 A | | 11/1996 | Barberich et al. |
| 5,589,511 A | | 12/1996 | Young, II et al. |
| 5,627,183 A | | 5/1997 | Gray, IV |
| 5,629,329 A | | 5/1997 | Gray et al. |
| 5,629,333 A | | 5/1997 | Young, III |
| 5,907,048 A | * | 5/1999 | Nishioka et al. ............ 549/356 |
| 6,114,548 A | * | 9/2000 | Newman et al. ............ 549/356 |

FOREIGN PATENT DOCUMENTS

CH              604 560         *   9/1978

OTHER PUBLICATIONS

Ubatullin, U.G, et al, Chem.Heterocycl. Compd (Eng.Transl) ; EN 20; 11; 1984; 1200–1202.
KGSSAQ; Khim.Geterosikl.Soedin.:RU;11; 1984; 1455–1457.
Aggarwal, Variner, et al, Teleay; Tetrahedron Lett.; EN; 38: 14; 1997; 2569–2572.

* cited by examiner

Primary Examiner—Jill Warden
Assistant Examiner—Monique T. Cole
(74) Attorney, Agent, or Firm—Joseph F. Leightner

(57) ABSTRACT

The present invention is directed to the use of an olfactory acceptable amount comprising tetrahydro-4-methylene-2-(4-methoxyphenyl)-2H-pyran, 5,6-dihydro-4-methyl-2-(4-methoxyphenyl)-2H-pyran, 3,6-dihydro-4-methyl-2-(4-methoxyphenyl)-2H-pyran and mixtures of these materials which are useful in creating fragrances, and scents in items such as perfumes, colognes and personal care products.

10 Claims, No Drawings

USE OF DIHYDROPYRANS AS FRAGRANCE MATERIAL

FIELD OF THE INVENTION

The present invention relates to the use of known chemicals, preferably employed as an isomeric mixture as a fragrance ingredient.

BACKGROUND OF THE INVENTION

There is an ongoing need in the fragrance industry to use new molecules to give perfumers and other persons ability to create new fragrances for perfumes, colognes and personal care products.

Various methyl methoxyphenyl-DH-pyran materials are disclosed in the art, see for example Ubatullin, U. G. et al., Chem.Heterocycl.Compd (Engl.Transl); EN 20; 11; 1984; 1200–1202; KGSSAQ; Khim.Geterosikl.Soedin.:RU;11; 1984; 1455–1457 and Aggarwal, Varinder et al., TELEAY; Tetrahedron Lett.; EN; 38:14; 1997 2569–2572. The methyl methoxyphenyl-DH-pyrans have not been used in the fragrance industry or reported to show utility as aroma chemicals or fragrance enhancers.

There is an ongoing need to provide new materials for use in fragrances.

SUMMARY OF THE INVENTION

The present invention is directed to the incorporating of an olfactory acceptable amount of the chemical selected from the group consisting of tetrahydro-4-methylene-2-(4-methoxyphenyl)-2H-pyran (compound I shown below), 5,6-dihydro-4-methyl-2-(4-methoxyphenyl)-2H-pyran (compound II shown below), 3,6-dihydro-4-methyl-2-(4-methoxyphenyl)-2H-pyran (compound III shown below) and mixtures of these chemicals. In a preferred embodiment of the invention the chemicals are provided in an olfactory acceptable amount as an isomeric mixture comprising 3–10% tetrahydro-4-methylene-2-(4-methoxyphenyl)-2H-pyran (compound I shown below), 35% 55% 5,6-dihydro-4-methyl-2(4-methoxyphenyl-2H-pyran 3,6-dihydro-4-methyl-methoxyphenyl)-2H-pyran (compound II shown below), and 35–55% 3,6-dihydro-4-methyl-2-(4-methoxyphenyl)-2H-pyran (compound III shown below) to enhance fragrance in perfumes, toilet waters, colognes, personal products and the like.

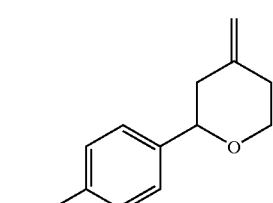

I

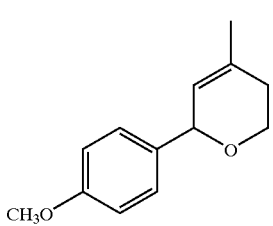

II

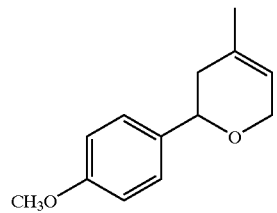

III

As described throughout the specification, the above mixture will be referred to as the methyl-4-methoxyphenyl-DH-pyrans.

DETAILED DESCRIPTION OF THE INVENTION

The present invention is directed to the use of the methyl-4-methoxyphenyl-DH-pyrans as a fragrance chemical. The odor characteristics of the methyl-4-methoxyphenyl-DH-pyran mixture is that of long lasting natural hay, caraway, basil, thymole, anine and spearmint notes reminiscent of the odor of methyl chavicol. Methyl chavicol, also known as p-allylanisole, is a very desirable odor profile having the following structure:

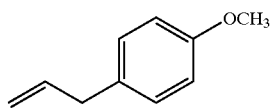

The methyl-4-methoxyphenyl-DH-pyran mixture is known in the art, see for example, Ubatullin, U. G. et al., Chem.Heterocycl.Compd (Engl.Transl); EN 20; 11; 1984; 1200–1202; KGSSAQ; Khim.Geterosikl.Soedin.:RU;11; 1984; 1455–1457 and Aggarwal, Varinder et al., TELEAY; Tetrahedron Lett.; EN; 38:14; 1997 2569–2572.

The mixture of the isomers can be separated using techniques well known in the art for the separation of isomeric mixtures, such techniques now being routinely used in the preparation of optically pure pharmaceuticals. Suitable techniques include, but are not limited to the use of isomerically pure intermediates, crystallization and preferably the use of chromatography techniques. Liquid or gas chromatography can be used, with gas chromatography being the preferred technique. U.S. Pat. Nos. 5,629,333; 5,629,329; 5,627,183; 5,589,511; 5,571,827; 5,561,151; 5,545,745; 5,532,278; 5,510,352; 5,508,279 and 5,492,933 are herein incorporated by reference as if set forth in their entirety, are just a few of the many patents that describe techniques for the separation of isomeric materials using various techniques.

Using these separation techniques, the yields of the individual compounds: tetrahydro-4-methylene-2-(4-methoxyphenyl)-2H-pyran; 5,6-dihydro-4-methyl-2-(4-methoxyphenyl)-2H-pyran; and 3,6-dihydro-4-methyl-2-(4-methoxyphenyl)-2H-pyran can exceed more than 80 weight percent, typically greater than about 90 and in preferred embodiments can exceed 95 weight percent of a desired isomer depending on the time and expense that is taken to isolate the desired compound. It is within the skill of those in the art to obtain greater than 99 weight percent of an individual isomer depending on the technique and time employed in the separation process.

The use of this material is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compound of the present invention can be used alone or in combination with other perfuming compositions, solvents, adjuvants and the like. The nature and variety of the other ingredients that can be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, typically from about 0.1 to about 9; preferably from about 0.5 to about 8 and most preferably from about 1 to about 7 weight percent. In addition to the compounds, other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art without departing from the scope of this invention. As used herein all percentages are weight percent and g is understood to be grams. IFF as used in the examples is understood to mean International Flavors & Fragrances Inc.

EXAMPLE 1

Use of the methyl-4-methoxyphenyl-DH-pyran mixture (approximately 10% by weight tetrahydro-4-methylene-2-(4-methoxyphenyl)-2H-pyran (approximately 45% by weight) 5,6-dihydro-4-methyl-2-(4-methoxyphenyl)-2H-pyran, and (approximately 45% by weight) 3,6-dihydro-4-methyl-2-(4-methoxyphenyl)-2H-pyran III in a herbal floral perfume

| Materials | Parts |
|---|---|
| TRIPLAL ® (IFF) | 0.2 |
| Amyl cinnamic aldehyde | 1.5 |
| Benzyl salicylate | 13.0 |
| GALAXOLIDE 50 ® (IFF) | 6.0 |
| GRISALVA ® (IFF) | 0.4 |
| HEDIONE ® (Firmenich) | 2.0 |
| Cis-3-hexenyl salicylate | 7.0 |
| Hexyl salicylate | 4.5 |
| ISO E SUPER ® (IFF) | 6.0 |
| Limonene | 3.0 |
| LYRAL ® (IFF) | 10.0 |
| Methyl-4-methoxyphenyl-DH-pyran mixture | 5.0 |
| PHENOXANOL ® (IFF) | 5.0 |
| PRECYCLEMONE B ® (IFF) | 0.4 |
| TOBACAROL ® (IFF) | 6.0 |
| VERAMOSS ® (IFF) | 1.6 |
| Dihydromyrcenol | 28.4 |
| TOTAL | 100.0 |

The above formulation was found to have a satisfactory fragrance long lasting notes that were enhanced by the presence of the methyl methoxyphenyl-DH-pyran mixture.

What is claimed is:

1. A method for improving, enhancing or modifying the odor properties of an article containing a fragrance by incorporating an olfactory acceptable amount of from about 3–10% weight percent tetrahydro-4-methylene-2-(4-methoxyphenyl)-2H-pyran, 35–55% weight percent 5,6-dihydro-4-methyl-2-(4-methoxyphenyl)-2H-pyran, and 35–55% weight percent 3,6-dihydro-4-methyl-2-(4-methoxyphenyl)-2H-pyran.

2. The method of claim 1 wherein the article into which the fragrance is incorporated into is selected from perfumes, colognes, toilet waters, personal care products, cleaning products and air fresheners.

3. The method of claim 2 wherein the cleaning product is selected from the group consisting of detergents, dishwashing compositions, scrubbing compounds and window cleaners.

4. The method of claim 2 wherein the article is a personal care product.

5. The method of claim 1 wherein the mixture of tetrahydro-4-methylene-2-(4methoxyphenyl)-2H-pyran, 5,6-dihydro-4-methyl-2-(4-methoxyphenyl)-2H-pyran, and 3,6-dihydro-4-methyl-2-(4-methoxyphenyl)-2H-pyran is provided at a level of from about from 0.005 to about 70 weight percent of the fragrance composition.

6. The method of claim 5 wherein the mixture of 3–10% tetrahydro-4-methylene-2-(4-methoxyphenyl)-2H-pyran, 35–55% 5,6-dihydro-4-methyl-2-(4-methoxyphenyl)-2H-pyran, and 35–55% 3,6-dihydro-4-methyl-2-(4-methoxyphenyl)-2H-pyran is provided at a level of from about from about 0.1 to about 50 of the fragrance composition.

7. The method of claim 6 wherein the mixture of 3–10% tetrahydro-4-methylene-2-(4-methoxyphenyl)-2H-pyran, 35–55% 5,6-dihydro-4-methyl-2-(4-methoxyphenyl)-2H-pyran, and 35–55% 3,6-dihydro-4-methyl-2-(4-methoxyphenyl)-2H-pyran is provided at a level of from about from about 0.2 to about 25 weight percent of the fragrance composition.

8. The method of claim 1 wherein the mixture of 3–10% tetrahydro-4-methylene-2-(4-methoxyphenyl)-2H-pyran, 35–55% 5,6-dihydro-4-methyl-2-(4-methoxyphenyl)-2H-pyran, and 35–55% 3,6-dihydro-4-methyl-2-(4-methoxyphenyl)-2H-pyran and mixtures thereof is provided at a level of from about 0.005 to about 10 weight percent of the fragranced article.

9. The method of claim 8 wherein the mixture comprised of 3–10% tetrahydro-4-methylene-2-(4-methoxyphenyl)-2H-pyran, 35–55% 5,6-dihydro-4-methyl-2-(4-methoxyphenyl)-2H-pyran, and 35–55% 3,6-dihydro-4-methyl-2-(4-methoxyphenyl)-2H-pyran is provided at a level of from about 0.1 to about 9 weight percent of the fragranced article.

10. The method of claim 9 wherein the mixture comprised of 3–10% tetrahydro-4-methylene-2-(4-methoxyphenyl)-2H-pyran, 35–55% 5,6-dihydro-4-methyl-2-(4-methoxyphenyl)-2H-pyran (II), and 35–55% 3,6-dihydro-4-methyl-2-(4-methoxyphenyl)-2H-pyran is provided at a level of from about 0.5 to about 8 weight percent of the fragranced article.

* * * * *